US009834613B2

(12) United States Patent
Skogen et al.

(10) Patent No.: US 9,834,613 B2
(45) Date of Patent: *Dec. 5, 2017

(54) PREPARATION USEFUL FOR, AND METHOD FOR TREATMENT OF NEONATAL ALLOIMMUNE THROMBOCYTOPENIA (NAIT)

(71) Applicant: PROPHYLIX PHARMA AS, Tromso (NO)

(72) Inventors: Bjorn Skogen, Tromso (NO); Anne Husebekk, Tromso (NO); Mette Kjaer, Tromso (NO); Jens Kjeldsen-Kragh, Eiksmarka (NO)

(73) Assignee: PROPHYLIX PHARMA AS, Tromso (NO)

( * ) Notice: Subject to any disclaimer, the term of this patent is extended or adjusted under 35 U.S.C. 154(b) by 0 days.

This patent is subject to a terminal disclaimer.

(21) Appl. No.: 15/089,449

(22) Filed: Apr. 1, 2016

(65) Prior Publication Data

US 2016/0215062 A1 Jul. 28, 2016

Related U.S. Application Data

(62) Division of application No. 14/478,484, filed on Sep. 5, 2014, now abandoned, which is a division of application No. 12/087,378, filed as application No. PCT/NO2006/000503 on Dec. 29, 2006, now Pat. No. 8,840,897.

(60) Provisional application No. 60/755,062, filed on Jan. 3, 2006.

(51) Int. Cl.
*A61K 39/395* (2006.01)
*C07K 16/34* (2006.01)
*C07K 16/06* (2006.01)
*A61K 39/00* (2006.01)

(52) U.S. Cl.
CPC .............. *C07K 16/34* (2013.01); *C07K 16/06* (2013.01); *A61K 2039/505* (2013.01); *A61K 2039/55* (2013.01); *C07K 2317/21* (2013.01); *C07K 2317/76* (2013.01)

(58) Field of Classification Search
None
See application file for complete search history.

(56) References Cited

U.S. PATENT DOCUMENTS

| 4,597,966 A | 7/1986 | Zolton .................. A61K 9/0019 424/141.1 |
| 6,203,706 B1 | 3/2001 | Schwind et al. |
| 8,840,897 B2* | 9/2014 | Skogen .................. C07K 16/06 424/139.1 |
| 2003/0027207 A1 | 2/2003 | Filpula |
| 2006/0172438 A1 | 8/2006 | Milunic et al. |
| 2007/0042949 A1 | 2/2007 | Urbankiak et al. |
| 2008/0261205 A1 | 10/2008 | Denomme |

FOREIGN PATENT DOCUMENTS

| CA | 2201283 A1 | 4/1996 |
| CN | 1282871 A | 2/2001 |
| JP | 2002122595 A | 4/2002 |
| WO | 9411740 A1 | 5/1994 |
| WO | 9610749 A1 | 4/1996 |
| WO | 9629600 A1 | 9/1996 |
| WO | 9855146 A1 | 12/1998 |
| WO | 2005002613 A1 | 1/2005 |

OTHER PUBLICATIONS

Bessos et al., Transfus Apher Sci. Dec. 2008;39(3):221-7. doi: 10.1016/j.transci.2008.09.006. Epub Oct. 21, 2008.*
Dunsmore, K P., BioDrugs. Oct. 1997;8(4):265-72.*
Kaplan C., Orphanet J Rare Dis. Oct. 10, 2006;1:39.*
Bessos et al. (Transfusion. Mar. 2003;43(3):350-6).
Joutsi-Korhonen, et al, "The effect of recombinant IgG antibodies against the leucine-33 form of the platelet B3 integrin (HPA-la) on platelet function", Thromb Haemost, 2004, pp. 743-754, vol. 91.
Peyruchaud, et al, "HPA-10wb (Laa): Genetic Determination of a New Platelet-Specific Alloantigen on Glycoprotein and Its Expression in COS-7 Cells", Blood, 1997, pp. 2422-2438, vol. 89, No. 7.
Proulx, et al, "Human Monoclonal Fab Fragments Recovered from a Combinatorial Library Bind Specifically to the Platelet HPA-1a Alloantigen on Glycoprotein IIb-IIIa", Vox Sanguinis, 1997, pp. 52-60, vol. 72.
Santoso, et al, "A naturally occurring Leu33Val mutation in B3-integrin impairs the HP-1a epitope: the third allele of HPA-1", Transfusion, 2006, pp. 790-799, vol. 46.
Bessos et al., Transfusion. Mar. 2003;43(3):350-6.
Bussel et al., Am J Obstet Gynecol. May 1996;174(5):1414-23.
Merriam Webster's Collegiate Dictionary, 10th edition, 1997, Merriam Webster, Inc., pp. 778 and 935.
Skogen et al, "Preparation and method of treatment of neonatal alloimmune thrombocytopenic purpura", U.S. Appl. No. 60/755,062, filed Jan. 3, 2006, published as priority document of U.S. Appl. No. 12/087,378 by USPTO and of PCT Appln. PCT/NO2006/000503 by World Intellectual Property Organization.
Mueller-Eckhardt et al., "348 cases of suspected neonatal alloimmune thrombocytopenia" The Lancet 363-6 (1989).
Kaplan et al., "Current trends in neonatal alloimmune thrombocytopenia: Diagnosis and therapy." In: Platelet Immunology: Fundamental and Clinical Aspects. Paris, John Libby Eurotext, Colloque Inserm. 206:267-78 (1991).
Spencer et al., "Feto-maternal alloimmune thrombocytopenia: a literature review and statistical analysis." Aust. NZJ Obstet Gynaecol. 41:45-55 (2001).

(Continued)

*Primary Examiner* — Michael Szperka
(74) *Attorney, Agent, or Firm* — Iphorgan Ltd.

(57) ABSTRACT

A preparation useful for, and a method for the prophylactic treatment of women post-childbirth in order to avoid immunization and antibody production, which could induce NAIT and fetal/neonatal bleeding in subsequent pregnancies comprising administering a preparation containing antibodies to HPA 1a within 72 hours after delivery in the first non-compatible pregnancy.

5 Claims, No Drawings

(56) References Cited

OTHER PUBLICATIONS

Altman "Diagnostic tests" In: Practical Statistics for Medical Research. London: Chapman & Hall. 1997:409-419.
Jaegtvik et al., "Neonatal alloimmune thrombocytopenia due to anti-HPA 1a antibodies; the level of maternal antibodies predicts the severity of thrombocytopenia in the newborn." Br J Obst Gynecol 107:691-4 (2000).
Kjeldsen-Kragh et al., "A screening intervention program aimed to reduce mortality and serious morbidity associated with severe neonatal alloimmune thrombocytopenia" Blood. 110(3):833-39 (2007).
Kjaer et al., "Human platelet antigen 1 (HPA 1) genotyping with 5' nuclease assay and sequence-specific primers reveals a single nucleotide deletion in intron 2 of the HPA 1a allele of platelet glycoprotein IIIa." Br J Haematology 117:405-08 (2002).
Randen et al., "Rapid and reliable genotyping of human platelet antigen (HPA)-1, -2, -3, -4, -5 a/b and Gov a/b by melting curve analysis." Transfusion 43:445-50 (2005).
Weiss et al., "A monoclonal antibody (SZ21) specific for platelet GPIIIa distinguishes PIA1 from PIA2." Tissue Antigens 46:374-81 (1995).
Killie et al., "Evaluation of a new flow cytometric HPA 1a screening method. A rapid and reliable tool for HPA 1a screening of blood donors and pregnant women." Transfusion and Apheresis Science 30:89-92 (2004).
Kiefel et al., Monoclonal antibody-specific immobilization of platelet antigens (MAIPA): A new tool for identification of platelet-reactive antibodies. Blood 70:1722-26 (1987).
Kiefel et al., "The MAIPA assay and its applications in immunohaematology." Transfusion Medicine 2:181-188 (1992) (Abstract).
Bertrand et al., "Quantification of human platelet antigen-1a antibodies with the monoclonal antibody immobilization of platelet antigens procedure." Transfusion 45:1319-23 (2005).
Kotsch et al,, "Sequencing of HLA class II genes based on the conserved diversity of the noncoding regions: sequencing based typing of HLA DRB genes." Tissue Antigens 53:486-97 (1999).
Valentin et al., "HLA DRw52a is involved in alloimmunization against PL-A1 antigen." Human Immunol. 27:73-79 (1990).
Davvkins, "Monitoring anti-HPA-1a platelet antibody levels during pregnancy using the MAIPA test." Vox Sang 68:27-34 (1995).
Goyenaga et al., "A HPA-1a negative woman immunized against HPA-1a antigen by platelet transfusions gave birth to a healthy HPA 1a positive child after disparition of the anti-HPA-1a at the end of the pregnancy. A case report." 7th European Symposium on Platelet, Granulocyte and Red Cell Immunobiology. Italy. Abstract, p. 109 (2002).
Birchall et al., "European collaborative study of the antenatal management of feta-maternal alloimmune thrombocytopenia." Br J Haematology 122:275-88 (2003).
National Institute for Clinical Excellence, "Guidance on the use of routine antenatal anti-D prophylaxis for RhD-negative women" NICE Technology Appraisal Guidance No. 41:1-16 (2002) ISBN: 1-84257-166-4.
Robson, "Use of Anti-D Immunoglobulin for Rh Prophylaxis (22)" Royal College of Obstetricians and Gynaecologists (2002)—pp. 1-6 of 6, www.rcog.org.uk.
Tiller H. et al., "Toward a Prophylaxis against Fetal and Neonatal Alloimmune Thrombocytopenta . . . ", Transfusion, 2012, vol. 52, pp. 1446-1457.
Killie , M.K. et al., "A Prospective Study of Maternal Anti-HPA 1a Antibody Level as a Potential Predictor of Alloimmune Thrombocytopenia in the Newborn", Haematologica, 2008, vol. 93, pp. 870-877.
Turner, M.L., Bessos, H. et al., "Prospective Epidemiologic Study of the Outcome and Cost-Effectiveness of Antenatal Screening . . . ", Transfusion, 2005, vol. 45, pp. 1945-1956.
Williamson, L.M. et al, "The Natural History of Fetomaternal Alloimmunization to the Platelet-Specific Antigen . . . ", Blood, 1998, vol. 92, pp. 2280-2287.
Allen D et al; "Collaborative study to establish the first international standard for quantitation of anti-HPA-1a", Vox Sanguinis 2005 United Kingdom, vol. 89, No. 2, 2005, pp. 100-104.
Dunsmore K P; "Intravenous immunoglobulin g therapy in fetal and neonatal alloimmune thromboctopenia", Biodrugs 1997, New Zealand, vol. 8, No. 4, 1997, pp. 265-272.
Radder, C M et al; "Effect of maternal anti-HPA-1a antibodies and polyclonal IVIG on the activation status of vascular endothelial cells", Clinical and Experimental Immunology, Jul. 2004, vol. 137, No. 1, pp. 216-222.
D. Lee et al, Transfusion Medicine (1999), 9, pp. 93-97, Blackwell Science Ltd.
Hodivala-Dilke et al; The Journal of Clinical Investigation, (1999), vol. 103, pp. 229-238.
Bessos et al; Transfusion and Apheresis Science (2008), 39, pp. 221-227, Science Direct, Elsevier Ltd.
European Patent Office (International Search Authority), International Search Report and Written Opinion, PCT/NO2006/000503, Apr. 3, 2007.
European Patent Office, European Search Report and Written Opinion, European Application No. 10190285.6, divisional of EPO national phase of PCT/NO2006/000503.

\* cited by examiner

PREPARATION USEFUL FOR, AND METHOD FOR TREATMENT OF NEONATAL ALLOIMMUNE THROMBOCYTOPENIA (NAIT)

CROSS-REFERENCE TO RELATED APPLICATIONS

This application is a continuing application of U.S. application Ser. No. 14/478,484, filed Sep. 5, 2014, which is a continuing application of U.S. application Ser. No. 12/087,378, filed Jul. 2, 2008, which is the national stage completion application of PCT Application Number PCT/NO06/00503, filed Dec. 29, 2006, which claims priority from U.S. Application No. 60/755,062, filed Jan. 3, 2006. Each of these applications is incorporated by reference herein in its entirety.

BACKGROUND

Field of the Invention

The invention relates to a preparation useful for, and a method for the prophylactic treatment of women post-childbirth in order to avoid immunization and antibody production, which could induce NAIT and fetal/neonatal bleeding in subsequent pregnancies.

Background of the Invention

Neonatal Alloimmune Thrombocytopenic Purpura. (NAITP)

Two percent of Caucasians are homozygous for human platelet antigen (HPA) 1b. The HPA 1a antigen is a potent immunogen and ten percent of pregnant HPA 1a negative women make antibodies to the HPA 1 antigen after immunization with their fetus' HPA 1a positive platelets. Most of these women have the major histocompatibility antigen HLA-DRB3*0101, but there are examples of women with other HLA DR antigens making the antibodies. The immunization can take place early in the first pregnancy making the fetus thrombocytopenic as early as the 16-20$^{th}$ week of gestation. Intracranial hemorrhage may be fatal, or the fetus can survive with neurological sequels. Fetal alloimmune thrombocytopenia is reported to be present in 1:1000-2000 pregnancies.

Most of the studies reporting frequencies of anti-HPA 1a antibodies have been done retrospectively in women giving birth to thrombocytopenic babies with Symptoms of impaired hemostasis. Recently a prospective study of 100 448 pregnant women showed a frequency of HPA 1bb of 2.1%. 10.6% of the women at risk had anti-HPA 1a antibodies and 55 babies had severe thrombocytopenia.

At present there is no general agreement about how to manage the follow-up of the pregnant women with anti-HPA 1a antibodies in order to reduce the risk for bleeding in the fetus/newborn. There is no reliable prenatal parameter to predict which fetuses that are susceptible to life-threatening thrombocytopenia and therefore need closer follow-up or intervention.

In order to approach the questions related to predictable tests for thrombocytopenia and management of the babies to reduce the risk of bleeding, we undertook a prospective investigation of samples from pregnant women referred to our laboratory at the Departments for immunology and transfusion medicine, University Hospital og Northern Norway and Ullevål University Hospital, for Rhesus D (RhD) testing.

Until now, the general opinion was that immunization with HPA 1a antigen took place during the first non-compatible pregnancy. Our research has disclosed, however, that in 70-80% of those women with antibodies to HPA 1a, immunization occurs in association with delivery, as antibodies can be detected 6 weeks post partum but not at the time of delivery. This is a very interesting observation, and shows that the time for immunization in NAIT is very similar to that seen in haemolytic disease of the newborn (HDN), contrary to the currently held belief in the art.

Hemolytic Disease of the Newborn (HDN).

A Rhesus D (RhD) negative woman with an RhD positive foetus, can make antibodies against the erythrocytes of her child if red cells enter her circulation. Her antibodies of the IgG class can transfer the placental barrier and destroy the red cells of the foetus. Hemolysis and anemia are the most common results of such antibody transfer, but the most feared complications are hydrops foetalis and death. In HDN, the immunization takes place when the first child is born, and antibodies to Rh(D) can be detected after termination of the pregnancy. Antibodies are not a problem in the first pregnancy, but may affect the next non-compatible child.

Today it is possible to prevent the generation of anti-Rh (D) antibodies in association with pregnancy. Within 72 hours after delivery, the woman is given an intramuscular injection of antibodies to the antigen, namely anti-Rh(D). The accepted explanation for the effect is that such antibodies will destroy or remove the fetal red cells that have passed into the circulation of the mother, and prevent immunization and the formation of antibodies to the Rh(D) antigen.

The antibody preparation is an IgG concentrate made from the plasma of individuals with anti-Rh(D) in their circulation. Normal individuals may have anti-Rh(D) as a consequence of insufficient prophylaxis with anti-Rh(D) in D-negative pregnant women, transfusion of Rh(D) positive blood to Rh(D) negative recipients, or as a result of active immunizations. "Rhesogamma P <<ZLB Behring>>" is a human immunoglobulin containing anti-D for prevention of HDN. 1.5 ml of the preparation contains 1500 IE (200 microgram) of anti-D, which makes up one therapeutic dose. The total amount of IgG in one dose is 255 mg. Ten doses are sold for the price of 3200 NOK.

A prerequisite for an efficient treatment is that the prophylaxis is given before the immune response is established in the mother. This is the case in HDN, as the immunization and antibody production takes place subsequent to the delivery of the first child. The treatment is very efficient, and HDN due to anti-D is seldom seen today.

Current Treatment of NAIT

At present, there is no prophylactic treatment for NAIT as is the case with HDN. Newborns with NAIT are treated with platelet transfusions or intravenous injections of gamma globulins after birth. If a woman delivers a child with severe NAIT, she may herself be treated with high dose intravenous IgG and/or steroids in her next pregnancy. In particular cases, the child may be transfused with compatible platelets several times during the second half of the pregnancy. This procedure is associated with a high mortality rate, about 1% in each puncture. These treatment modalities are only eligible when the woman has given birth to a thrombocytopenic child in a previous pregnancy. So, the first child is born without any kind of precautionary action. Other postnatal treatment may anyhow come too late, as the damage to the child may occur during delivery or shortly after.

SUMMARY OF THE INVENTION

The current opinion in this field is that the immunization of the mother occurs during, and not after the first non-compatible pregnancy. Therefore, prophylactic treatment has not been an option. Now, with our surprising observation that immunization, in about 70-80% of cases, takes place after the first non-compatible pregnancy, there is good reason to believe that also this condition could be influenced by a similar treatment as is used for HDN.

Rh(D) negative women giving birth to Rh(D) positive children, have the risk to produce antibodies to the Rh(D) antigen present on the childs erythrocytes. The stimulation to such antibody production, is a result of fetal erythrocytes entering the mothers circulation in association with delivery. The crucial point is that the mother has not been stimulated with fetal erythrocytes during the pregnancy, so that the first stimulus she receives, is that resulting from fetal erythrocytes at delivery. If the mother is given antibodies to Rh(D) after she has received the Rh(D) positive fetal erythrocytes into her circulation, but before her immune system starts to produce her own antibodies to Rh(D), this production is blocked. It is believed that the injected antibodies bind to the Rh(D) positive fetal erythrocytes and destroy them before they are able to stimulate the mothers immune system to antibody production.

According to one aspect of the invention, we can substitute Rh(D), erythrocytes and antibodies to Rh(D), with HPA 1a, platelets and antibodies to HPA 1a, respectively.

HPA 1a negative women giving birth to HPA 1a positive children, have the risk to produce antibodies to the HPA 1a antigen present on the child's platelets. The stimulation to such antibody production, is a result of fetal platelets entering the mothers circulation in association with delivery. The crucial point is that the mother has not been stimulated with fetal platelets during the pregnancy, so that the first stimulus she receives, is that resulting from fetal platelets at delivery. If the mother is given antibodies to HPA 1a after she has received the HPA 1a positive fetal platelets into her circulation, but before her immune system starts to produce her own antibodies to HPA 1a, this production will be blocked. It is believed that the injected antibodies will bind to the HPA 1a positive fetal platelets and destroy them before they are able to stimulate the mothers immune system to antibody production.

Accordingly, the current invention provides for a prophylactic regime similar to that for HDN but applied for the prophylactic treatment of NAIT.

An immunoglobulin fraction containing antibodies to HPA 1a can be isolated from individuals with high levels of the antibody. Women who have such antibodies as a result of previous incompatible pregnancies, would be the most preferred donors. The preparation is made by isolation of total IgG from human plasma containing anti-HPA 1a. A therapeutic dose of 0.5-2.0 ml, preferably 1.5 ml containing 250-300 mg IgG, is administered by injection as soon as possible after delivery, and at latest within 72 hours. The injection is given once.

DETAILED DESCRIPTION OF THE INVENTION

Based upon the unpublished research of the inventors described in U.S. provisional patent application 60/755,062 filed 3 Jan. 2006, the entire contents of which are incorporated by reference as if fully repeated herein, it has been surprisingly discovered that in 70-80% of pregnant women with antibodies to HPA 1a, immunization occurs in association with delivery as opposed to during the first non-compatible pregnancy. This conclusion is based upon the observation of subjects where antibodies can be detected 6 weeks post partum but not at the time of delivery. This is a very interesting observation, and shows that the time for immunization in NAIT is very similar to that seen in haemolytic disease of the newborn (HDN), contrary to the currently held belief in the art. Based upon this correlation with HDN, the present invention provides a preparation useful for, and a method of treatment of NAIT that similar to that for HDN.

The Preparation

It is current practice today to fractionate IgG from normal blood donor plasma for the treatment of immunodeficiency. Plasma is collected in the blood banks, and fractionation is performed by a collaborating company. The immunoglobulin preparation is accepted for use by Statens Legemiddelverk (The Norwegian Government body regulating pharmaceuticals).

For the purpose of the present invention it is preferable to select donors with high levels of anti-HPA 1a. In the context of the invention, donors with "high levels" are preferably women who have given birth to children with NAIT, who in 80-90% of cases, have anti-HPA 1a levels above 200 AU/ml. To define arbitrary units (AU), we selected a serum from a woman who had a child with severe thrombocytopenia. Her serum was given the quantity of anti-HPA 1a of 1000 AU/ml. This serum is used to create a standard curve for quantitation of other women's antibody levels. According to the invention, we select sera from women with "high levels" (>1000 AU/ml) for production of IgG for the prophylactic preparation.

Based upon the above criteria, enough plasma is collected to make up a processable batch. The batch is thereafter fractionated by methods known in the fractionation industry. Such methods include isolating Immunoglobulin G from plasma by ion exchange chromatography or immunoadsorption techniques or by adsorption to protein A-Sepharose.

1 liter of plasma yields about 4.0 g IgG, and 1 therapeutic dose of anti-D consists of about 255 mg IgG. If we assume that the same amount of IgG from anti-HPA 1a plasma would be sufficient for 1 therapeutic dose, it means that 1 liter of plasma will give 16 therapeutic doses containing from about 100-400, preferably from 200-300 mg IgG.

In order to make sure that the preparation contains antibodies to HPA 1a in sufficient amounts, we will perform neutralization experiments with intact platelets. Comparison with the anti-D preparation that is used for HDN prophylaxis will give an indication of the potential of the given anti-HPA 1a preparation. Preparations of IgG with either anti-Rh (D) or anti-HPA 1a at a certain IgG concentration (250 mg/ml) is mixed with defined amounts of erythrocytes or platelets with the corresponding antigens on the surface. By mixing different amounts of platelets and erythrocytes to the antibody preparations, it can be determined exactly how much platelets or erythrocytes that is required to neutralize the respective antibodies in the two different IgG preparations. Platelets and erythrocytes have defined amounts (numbers) of antigens on the surface; therefore it can be determined how many antibodies of the respective specificities that are present in each preparation. By adjustments of the IgG concentration in each preparation, equimolecular solutions with regard to antibody molecules can be made. In this way we intend to make a preparation of anti-HPA 1a that contains as many specific antibody molecules as the anti-Rhesus(D) preparation. The hypothesis is that the same number of antibody molecules has the same potential to block the immune response.

An advantage of a the preparation made by the above-describe method is that it will be easily approved for use, and will not need to go through the whole time consuming registration process that is mandatory for the introduction of new drugs.

Product Characterization:

The preparation according to the invention comprises a concentrate made by the isolation of total IgG from human plasma. The preparation contains representative amounts of all antibody specificities that are present in the actual sera collected for processing. In addition to this, the preparation contains IgG antibodies specific for HPA 1a at sufficient levels to inhibit an immune response in a subject to HPA 1a antigens. Those antibodies will comprise an amount of the total IgG of from about 0.1% to 2% by weight. The antibodies are dissolved in saline containing preservatives.

Therapeutic Dose:

A therapeutic dose is between 0.5 ml-2.0 ml of the preparation, preferably 1.5 ml. 1.5 ml of the preparation contains specific antibodies to HPA 1a. One therapeutic dose contains over 200 mg IgG, preferably from 250-300 mg IgG.

Prevention of Immunization with HPA 1a Positive Platelets

The target individuals for the injections are women, immediately after delivery in their first pregnancy. If they have been exposed to the antigen at an earlier occasion, the effect of the treatment could be minimal.

To trace the target individuals, one aspect of the invention provides for a screening procedure. If 50,000 pregnants are genotyped for the HPA 1 antigen, we will find about 1,000 HPA 1a negative women. About 400 of those are primigravidae, and it is expected that about 40 of them will make antibodies to HPA 1a. 10 will make antibodies during the pregnancy, and 30 after delivery.

The object for the treatment according to the invention is to reduce the number of women that make antibodies after delivery. The women who have antibodies at time of delivery will not be treated. For the 30 who make antibodies after delivery, we expect to block the immune response in 90% of the cases.

Administration

One therapeutic dose of the preparation according to the invention is injected intramuscularly as soon as possible, and within 72 hours after delivery.

Frequency of Injection

The injection is given once.

Frequency of Treatments in Norway Per Year

About 70,000 pregnancies are initiated each year in Norway. This figure includes normal deliveries, spontaneous and provoked abortions. If 2.1% of all Caucasians are HPA 1a negative, this means that about 1,500 pregnants have to be treated each year. Another possible indication for prophylaxis is HPA 1a negative women at fertile age that are transfused with HPA 1a positive blood. This would be between 200 and 400 patients each year.

Example: Confirmation of Effectiveness of Treatment

Antibodies 6 weeks after delivery.

About 1,000 HPA 1a negative women will be identified. About 400 of those are primigravidae, and it is expected that about 40 of them will make antibodies to HPA 1a. 10 will make antibodies during the pregnancy, and 30 after delivery. Our goal is to reduce the number of women that make antibodies after delivery. Those women who have antibodies at time of delivery will not be treated. The 370 primigravidae with no detectable anti-HPA 1a at delivery will be treated. Antibody levels will be analysed 6 weeks after delivery. For the 30 who normally are expected to make antibodies 6 weeks after delivery, we do not expect to find anti-HPA 1a antibodies in 70-90% of them after treatment.

The invention claimed is:

1. A method for the prophylactic treatment of neonatal alloimmune thrombocytopenia (NAIT), the method comprising the step of:
   administering to a woman who is negative for the human platelet antigen HPA 1a, as well as negative for antibodies specific to the human platelet antigen HPA 1a, and who is pregnant with an HPA 1a positive fetus,
   a preparation comprising a sufficient quantity of antibodies to HPA 1a so as to substantially inhibit the woman's immune system from producing antibodies to HPA 1a,
   wherein the preparation is prophylactically injected into the woman such that the injected antibodies will bind to any HPA 1a positive fetal platelets which she receives or has received into her circulation from her HPA 1a positive fetus, before her own immune system starts to produce antibodies to the HPA 1a antigen on the fetal platelets.

2. The method of claim 1, wherein the preparation comprises Immunoglobulin G plasma derived from human plasma.

3. The method of claim 1, wherein the preparation that is administered comprises an Immunoglobulin G (IgG) concentrate derived from human plasma containing antibodies specific to human platelet antigen HPA 1a.

4. The method of claim 1, wherein the preparation comprises 100-400 μg anti-HPA 1a antibodies.

5. The method of claim 1, wherein the preparation comprises 200-300 μg anti-HPA 1a antibodies.

* * * * *